United States Patent

Schmidt et al.

[11] Patent Number: 6,001,073
[45] Date of Patent: Dec. 14, 1999

[54] DEVICE FOR INDUCING ALTERNATING TACTILE STIMULATIONS

[76] Inventors: Jurgen G. Schmidt; Shirley Jean Schmidt, both of 8819 Welles Edge, San Antonio, Tex. 78240-4905

[21] Appl. No.: 08/943,844

[22] Filed: Jul. 22, 1997

[51] Int. Cl.$^6$ ..................................................... A61H 1/00
[52] U.S. Cl. ................................ 601/72; 601/46; 601/48; 601/67; 601/69; 340/825.19; 434/114
[58] Field of Search .............................. 601/80, 67, 69, 601/70, 72, 81, 40, 46, 47, 48, 54, 60, 78, 56, 57, 133, 134; 434/114, 116, 236, 258; 340/825.19; 351/240, 239

[56] References Cited

U.S. PATENT DOCUMENTS

| | | | |
|---|---|---|---|
| 2,830,578 | 4/1958 | Groff | 601/47 |
| 3,869,812 | 3/1975 | Arakelian et al. | 434/258 |
| 3,984,708 | 10/1976 | Holmlund et al. | 601/80 |
| 3,986,136 | 10/1976 | Hurlburt | 434/236 |
| 4,232,661 | 11/1980 | Christensen | 601/48 |
| 4,343,303 | 8/1982 | Williams | 601/46 |
| 4,581,491 | 4/1986 | Boothroyd | 434/114 |
| 4,732,140 | 3/1988 | Stoffregen | 601/71 |
| 4,779,615 | 10/1988 | Frazier | 601/48 |
| 4,788,968 | 12/1988 | Rudashevsky et al. . | |
| 5,106,159 | 4/1992 | Iwamoto | 297/411.27 |
| 5,113,852 | 5/1992 | Murtonen | 601/47 |
| 5,165,897 | 11/1992 | Johnson | 434/113 |
| 5,188,096 | 2/1993 | Yoo | 601/57 |
| 5,195,532 | 3/1993 | Schumacher et al. | 601/101 |
| 5,304,112 | 4/1994 | Mrklas et al. | 434/236 |
| 5,343,261 | 8/1994 | Wilson . | |
| 5,388,992 | 2/1995 | Franklin et al. | 434/114 |
| 5,437,607 | 8/1995 | Taylor | 601/57 |
| 5,437,608 | 8/1995 | Cutler | 601/48 |
| 5,486,156 | 1/1996 | Takach . | |
| 5,519,292 | 5/1996 | Taylor et al. | 601/80 |
| 5,601,529 | 2/1997 | Wollman | 601/70 |
| 5,611,771 | 3/1997 | Taylor | 601/48 |
| 5,619,181 | 4/1997 | Murray . | |
| 5,619,291 | 4/1997 | Putnam | 351/240 |
| 5,730,707 | 3/1998 | Vang | 601/70 |
| 5,762,618 | 6/1998 | Yamanaka et al. | 601/148 |

OTHER PUBLICATIONS

Francine Shapiro, Ph.D. 1995 "Eye Movement Desensitization and Reprocessing, Basic Principles, Protocols, and Procedures", The Guilford Press, New York, London.

*Primary Examiner*—Jerome W. Donnelly
*Assistant Examiner*—Justine R. Yu
*Attorney, Agent, or Firm*—Arnold White & Durkee

[57] ABSTRACT

A device for inducing alternating tactile stimulations in a human subject is disclosed. The device includes a first vibrating element and a second vibrating element connected to a controller. The subject holds the first vibrating element in one hand and the second vibrating element in the other hand. When the device is activated the following occurs in sequence: the first vibrating element vibrates, pauses, the second vibrating element vibrates, pauses, the first vibrating element vibrates, pauses, the second vibrating element vibrates, pauses, and so forth, until the device is deactivated. The first and second vibrating elements are preferably of a hand-held size and shape. The controller has several operating features including: (a) a vibration-duration control which regulates and controls the duration, and thereby intensity, of vibrations (typically 50 to 200 milliseconds), and (b) a pause-duration control which regulates and controls the length of the pause between vibrations (typically 100 to 2000 milliseconds). The controller has a visual display module with: (a) left and right blinking indicators which are synchronized to the activation of the first and second vibrating elements, and (b) a counter display which shows a count of the number of times the first and second vibrating elements have cycled.

20 Claims, 4 Drawing Sheets

DEVICE FOR INDUCING ALTERNATING TACTILE STIMULATIONS

BACKGROUND

1. Field of Invention

The present invention is a device for inducing alternating tactile stimulations in a subject. Post-traumatic stress disorder (PTSD) is generally characterized by anxiety attacks, sleep disturbances, flashbacks, and other symptoms which relate to a prior traumatic event. PTSD is particularly common to victims of physical and sexual assault, and to war veterans. Traditional treatments for PTSD, such as "flooding" and "systematic desensitization" have met with limited success.

Recently a new treatment for PTSD was discovered, Eye Movement Desensitization and Reprocessing (EMDR), where the EMDR therapist instructs the client to recall a picture from the traumatic event, identify related negative thoughts/beliefs, notice associated body sensations, and move their eyes rapidly back and forth. Before, during and after this procedure the client is asked for their subjective level of disturbance. It has been found that after EMDR treatment, traumatized clients report significantly reduced levels of PTSD symptoms.

There are three variations of the EMDR procedure. The first variation is the procedure as stated above, using rapid eye movements. The other two variations are identical to the above in every way except that they involve alternatives to rapid eye movements. One variation involves the use of soft, alternating tones. For example, tone in right ear, then left ear, then right ear, then left ear and so forth. The other variation involves the use of gentle, alternating tactile stimulation of the client's hands, knees, shoulders, feet, or other bilateral body parts. For example, the therapist can gently touch the client's right hand, left hand, right hand, left hand, and so forth. All three EMDR procedure variations (rapid eye movements, alternating tones, and alternating tactile stimulations) appear to produce the same beneficial treatment effects.

Clients tend to have a preference for one variation or another. Some will choose one because they like it, or because they do not like the alternatives. For example, some clients prefer to process their traumatic memories with eyes closed (ruling out eye movements), and some prefer processing trauma in a quiet environment (ruling out alternating tones). Some clients prefer the tactile stimulation because it helps them feel more grounded. Sometimes intense crying interferes with the client's ability to maintain rapid eye movements making it necessary to switch to tones or tactile stimulations in mid-session. Children may have attention spans too short for processing trauma with eye movements, necessitating an alternative. Client handicaps, such as blindness or deafness, may also rule out one or more procedure variations. It is recommended that EMDR therapists be flexible and open to the varying needs and preferences of clients when deciding which variation to use at a given moment. All three variations are useful and have a necessary place in EMDR therapy.

2. Discussion of Prior Art

Most clients find it difficult to maintain rapid eye movements without assistance. Because of this, clients are usually asked to track the therapist's hand or fingers moving rapidly back and forth across the client's field of vision. Some therapists have reported disadvantages to this method, such as difficulty maintaining constant both rate of speed and straightness of path. A device for overcoming this problem has been invented by David L. Wilson (U.S. Pat. No. 5,343,261, Aug. 30, 1994). Wilson's device for inducing saccadic eye movements involves a series of evenly-spaced light emitting diodes (LEDs) on a horizontal bar. In use, the LEDs blink on and off in a linear sequence, back and forth across the bar. By tracking the blinking LEDs many clients can easily maintain the rapid eye movements. Wilson's invention also includes a means for generating alternating tones.

While Wilson's invention is useful, it only assists EMDR therapists with two of the three EMDR procedure variations, and does not induce alternating tactile stimulations. Currently EMDR therapists manually induce them by tapping on the client. There are several disadvantages to doing this:

(a) The therapist has to lean over to physically touch the client. A full session of bending over may require that the therapist maintain an uncomfortable posture for a prolonged period. (EMDR sessions are typically 1–2 hours long.) Over days, weeks, and months this can lead to chronic discomfort and muscle strain.

(b) During EMDR therapy, the therapist must pay attention to both verbal and non-verbal communications from the client. It is sometimes difficult to do this while counting right and left taps. (The standard EMDR protocol has recommended guidelines for the number of saccadic eye movements, tones, or taps in a treatment set.)

(c) Some clients feel threatened when touched. If a therapist taps on such a client he/she risks compromising the therapeutic alliance and ultimately client progress.

(d) Some clients may construe the therapist's touch as a sexual overture, leaving clinicians vulnerable to complications in the therapeutic process and possibly lawsuits.

SUMMARY

The present invention offers a simple and easy way for inducing alternating tactile stimulations in a human subject. The device includes a first vibrating element and a second vibrating element connected to a controller. The subject holds the first vibrating element in one hand and the second vibrating element in the other hand. When the device is activated the following occurs in sequence: the first vibrating element vibrates, pauses, the second vibrating element vibrates, pauses, the first vibrating element vibrates, pauses, the second vibrating element vibrates, pauses, and so forth, until the device is deactivated. The controller has several operating features including: (a) a vibration-duration control which regulates and controls the duration of vibrations (typically 50 to 200 milliseconds), and (b) a pause-duration control which regulates and controls the length of the pause between vibrations (typically 100 to 2000 milliseconds). The controller has a visual display module with: (a) left and right blinking indicators which are synchronized to the activation of the first and second vibrating elements, and (b) a counter display which shows a count of the number of times the first and second vibrating elements have cycled.

The advantages of using this invention are as follows:

(a) A therapist using this device can sit in a comfortable and relaxed posture instead of holding, for extended periods, the awkward postures necessary for manually tapping on clients.

(b) During each treatment set the invention counts and clearly displays the number of induced tactile stimulations for the therapist. Therefore, a therapist using this device can focus entirely on listening to and watching the client. No additional attention is needed for counting.

(c) With this device a therapist can induce alternating tactile stimulations with clients who might otherwise feel threatened by the therapist's touch.

(d) With this device a therapist can induce alternating tactile stimulations in a non-intimate, non-personal way. Therefore, clients will be unlikely to perceive the implementation of this EMDR procedure variation as a sexual overture.

(e) A therapist can adjust the device's duration and pause controls to suit the individual preferences of clients.

The present invention provides a simple device an EMDR therapist can use to induce alternating tactile stimulations without touching the client and constitutes a welcome advance to the field of psychotherapy.

DESCRIPTION—FIGS. 1,2,3,4

Figure 1A:
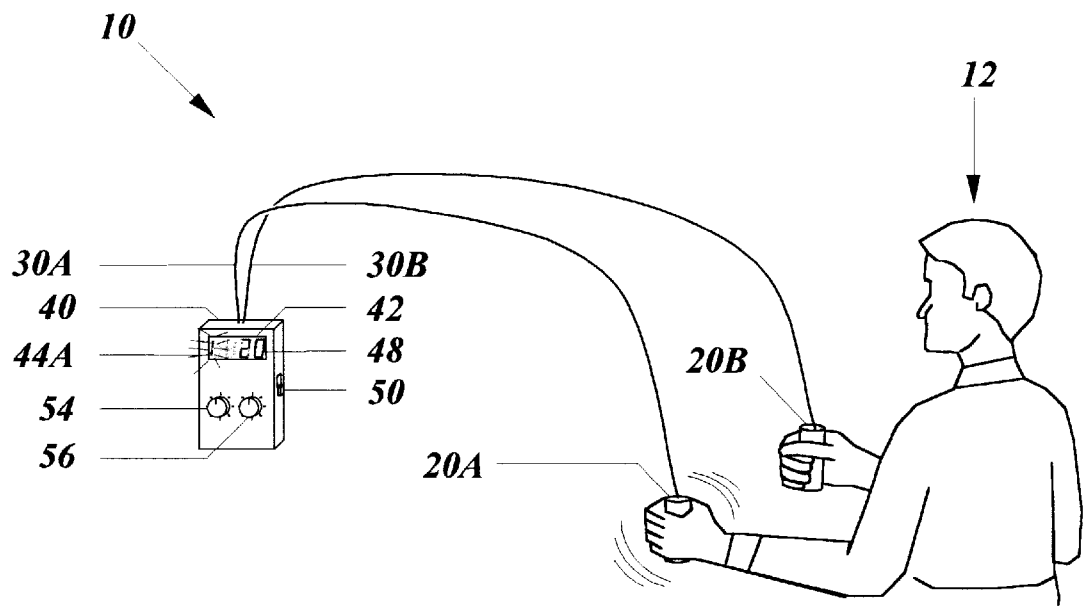
FIG. 1 shows a perspective view of the device for inducing alternating tactile stimulations in a human subject.
Figure 1B:
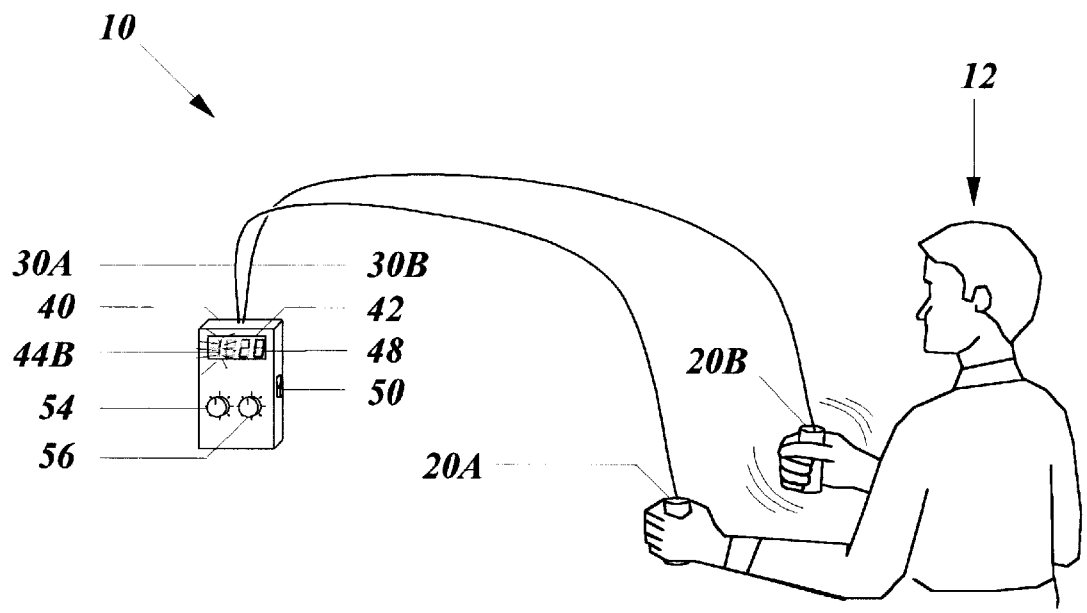

FIG. 1 shows a device 10 inducing alternating tactile stimulations in a subject 12 who is holding a first vibrating element 20A and a second vibrating element 20B. The first vibrating element 20A is connected to a controller 40 by a first electrical connection 30A and the second vibrating element 20B is connected to the controller 40 by a second electrical connection 30B. The controller 40 houses a power switch 50, a vibration-duration control 54, a pause-duration control 56, and a visual display module 42. The visual display module 42 has two important features:

(a) it has a left blinking indicator 44A and a right blinking indicator 44B which are synchronized with the activation of the first and second vibrating elements 20A and 20B respectively; and (b) it has a digital counter display 48 which displays the number of times the first and second vibrating elements 20A and 20B have been activated since switching on the power.

Figure 2:
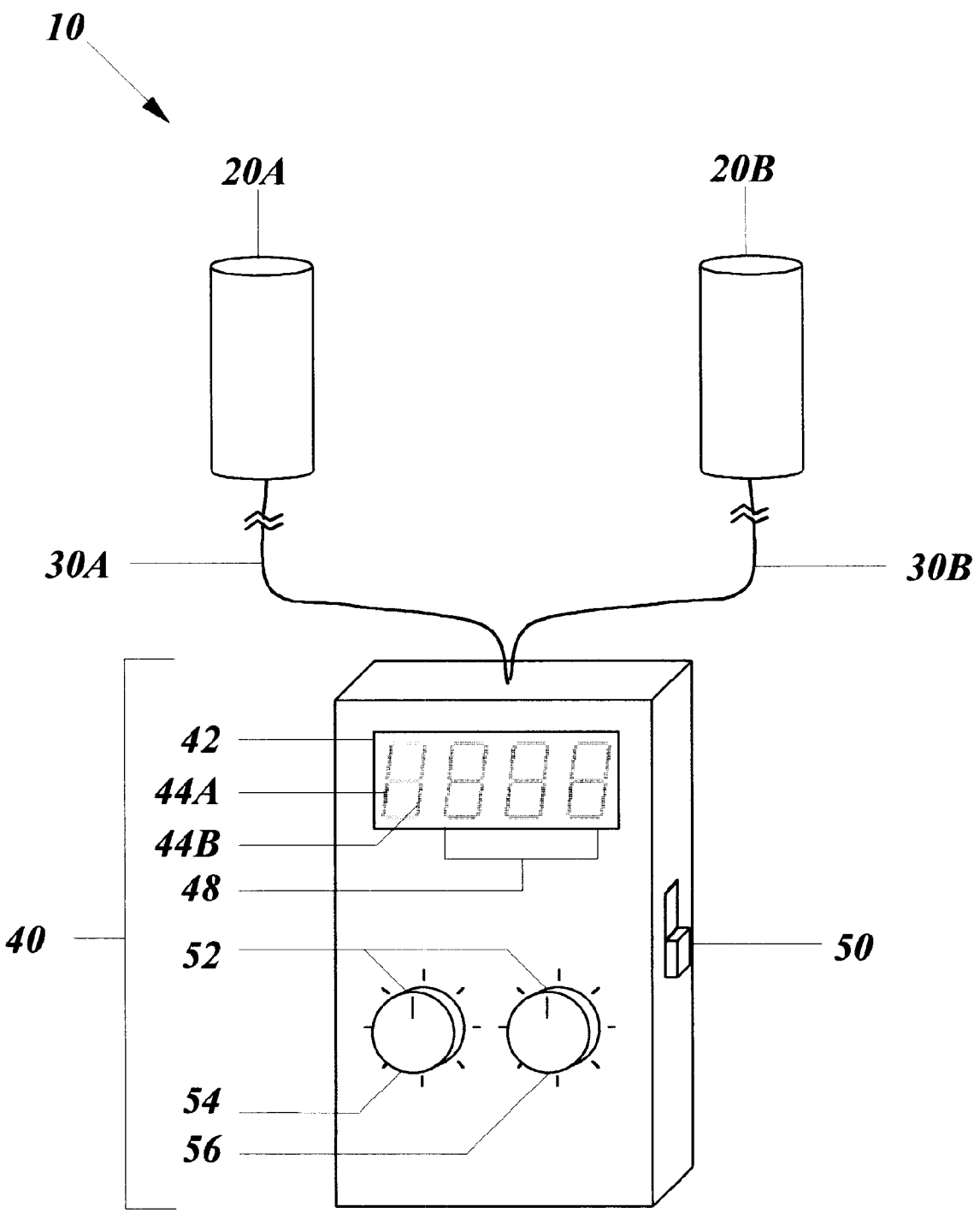
FIG. 2 is a perspective view of the device.

FIG. 2 shows a close-up perspective view of the device 10. The first and second vibrating elements 20A and 20B are connected to the controller 40 by the first and second electrical connections 30A and 30B. The controller 40 houses the power switch 50, operating controls 52, and the visual display module 42. The visual display module 42 may consist of four 7-segment numeric light emitting diode (LED) digits. Three of these digits comprise the digital counter display 48. Segments of the fourth digit comprise the left and right blinking indicators 44A and 44B, which are synchronized with the activation of the first and second vibrating elements 20A and 20B respectively. Operating controls 52 consist of a vibration-duration control 54 and a pause-duration control 56 (FIG. 4).

Figure 3:
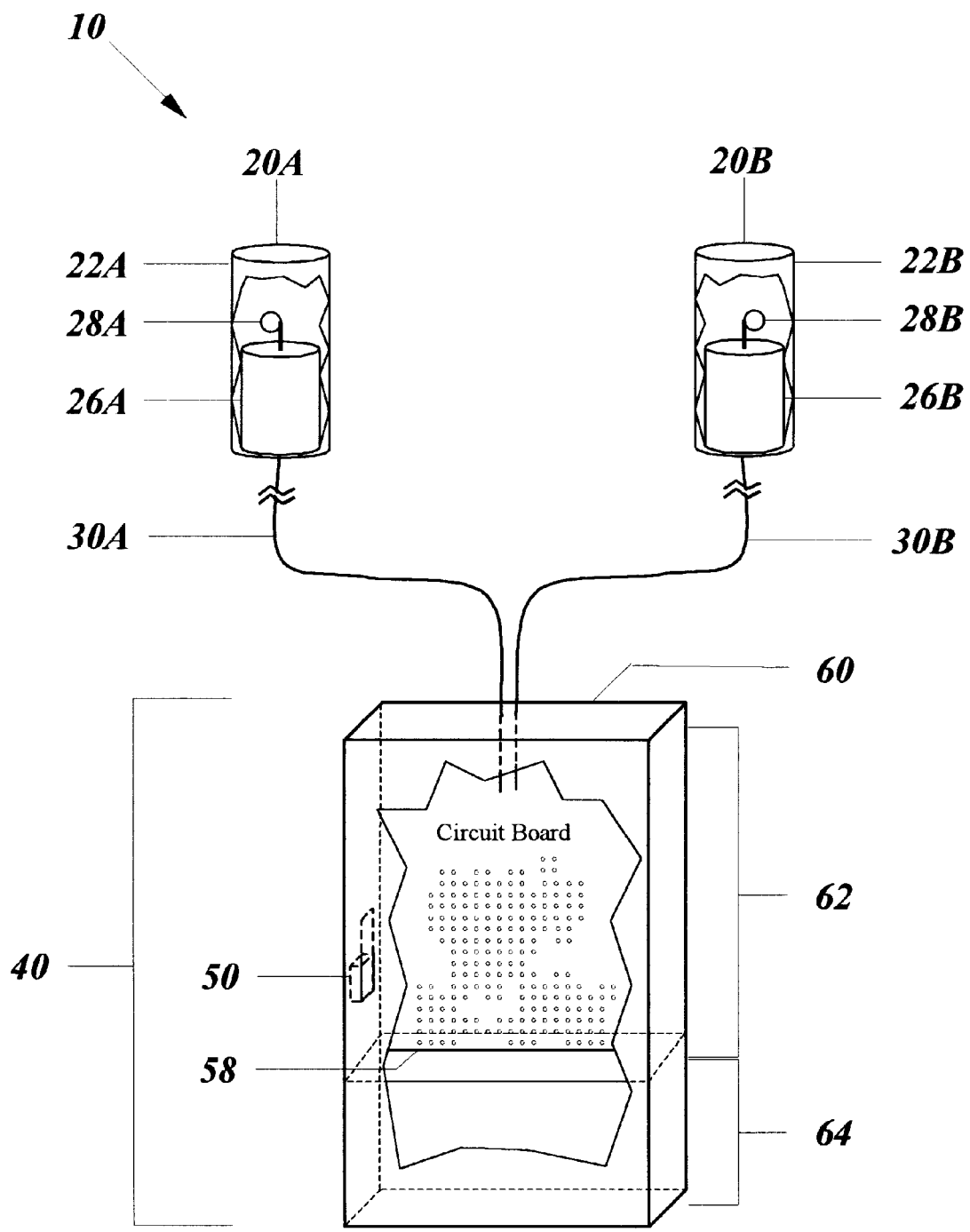
FIG. 3 provides a perspective view of the device, with a cutaway view of the first and second vibrating elements, and a cutaway view of the back of the controller.

FIG. 3 shows a cutaway view of the first and second vibrating elements 20A and 20B. The first vibrating element 20A is comprised of a first enclosure 22A made of plastic or metal, preferably cylindrical in shape and of a size to be easily held in a person's hand. Firmly attached within the first enclosure 22A is a first electric motor 26A. A first off-center weight 28A is firmly attached to the shaft of the first electric motor 26A. The first electric motor 26A is connected to the controller 40 by the first electrical connection 30A. FIG. 3 illustrates that the construction of the second vibrating element 20B is identical to the construction of the first vibrating element 20A. The electrical connections 30A and 30B consist of insulated electrical wire having two conductors each. The preferred length of the electrical connections 30A and 30B is approximately two meters to allow for a comfortable distance between operator and subject 12.

FIG. 3 also shows a cutaway view of the back of the controller 40. A controller enclosure 60 is preferably constructed of a rigid material such as wood, plastic or metal, and is preferably of a size to be conveniently held in one or both hands. The controller enclosure 60 has two compartments, an electronics compartment 62, and a battery compartment 64. The electronics compartment houses a circuit board 58. The power switch 50 on the controller 40 is connected to a power source 70 (FIG. 4), preferably batteries contained in the battery compartment 54.

Figure 4:
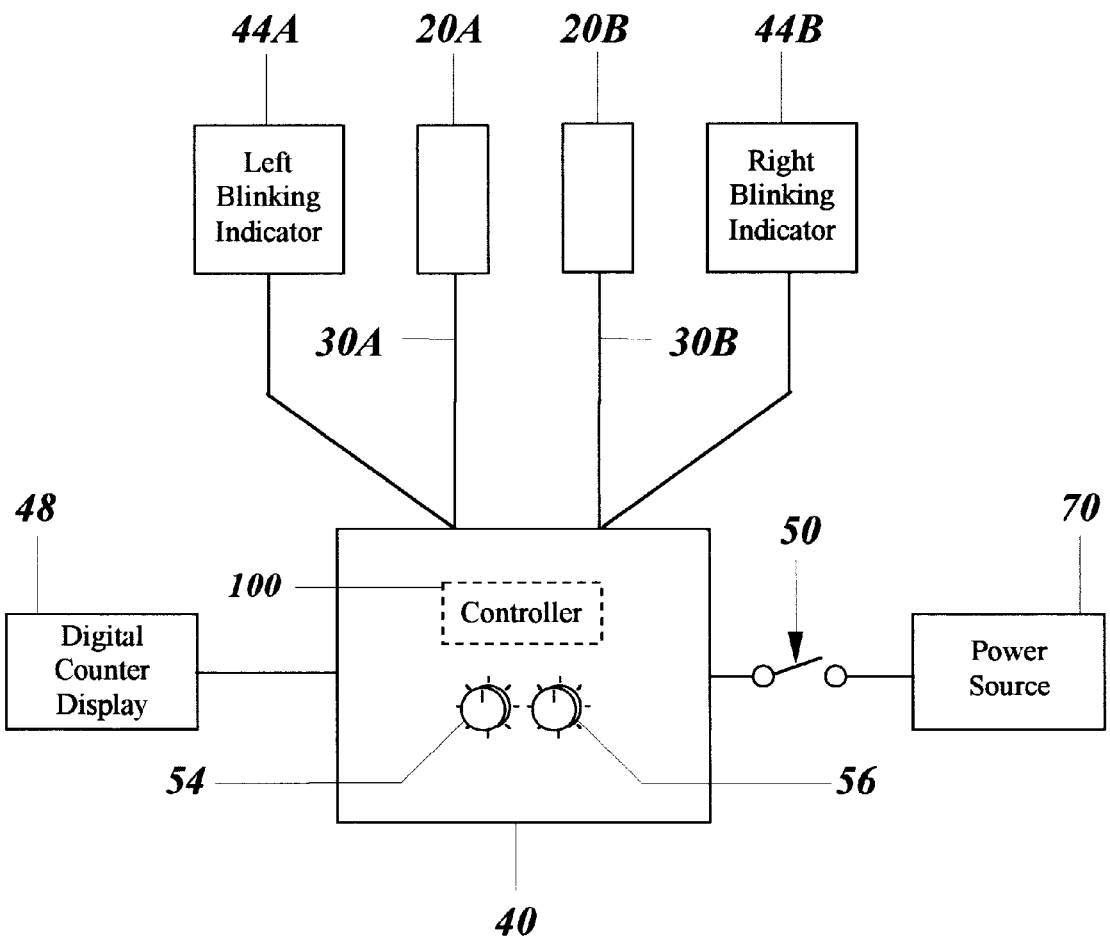
FIG. 4 is an electrical block diagram of the device.

Referring now to FIGS. 1 and 4, the subject 12 can be seen placed in contact with the first and second vibrating elements 20A and 20B (FIG. 1), for example, by holding one in each hand. Other forms of bodily contact are also acceptable as long as they occur on opposite sides of the body, for example, against each thigh or against each forearm. The person controlling the device 10, usually a therapist, activates device 10 by turning on power switch 50.

FIG. 4 illustrates the operation of the invention by way of an electrical block diagram. When the power switch 50 is closed, power travels to the controller 40 and activates the programmable micro-controller 100 (FIG. 4). The controller 40 directs the first and second vibrating elements 20A and 20B to begin vibrating, starting with the first vibrating element 20A and then the second vibrating element 20B, and so forth, in an alternating fashion. When the first vibrating element 20A is activated, the left blinking indicator 44A illuminates, and when the second vibrating element 20B is activated, the right blinking indicator 44B illuminates. The activation of the first vibrating element 20A, followed by a pause, and the activation of the second vibrating element 20B, followed by a pause, constitutes an "activation cycle." During operation, the digital counter display 48 shows an updated count of activation cycles, up to a maximum of 999. Every time the power switch 50 is turned on the counting begins at 0. Once the digital counter display 48 reaches 999 it resets to 0 and begins counting again. By operating the vibration-duration control 54 the therapist can increase or decrease the duration of the vibrations during an activation cycle, with the duration ranging from 5 to 300 milliseconds, but more preferably 50 to 200 milliseconds. This essentially controls the intensity of the tactile stimulation which is simply a function of how long the first and second vibrating elements 20A and 20B are activated. By operating the pause-duration control 56, the operator can increase or decrease the amount of time between the end of one vibration and the start of the next, with the pause length ranging from about 50 to 4000 milliseconds, but more preferably 100 to 2000 milliseconds. This essentially controls the cycling frequency, since shorter pauses means more rapid cycling than longer pauses. Table 1 defines an exemplary control logic sequence programmed into the programmable micro-controller 100:

Table 1
  Start:
  Initialize Counter to Zero
  Turn Off Visual Display
  Turn Off Motors
  Cycle:
  Read Resistance Value of Vibration-duration Control and store in Vibration_Value
  Read Resistance Value of Pause-duration Control and store in Pause_Value
  Activate First Motor and Left Light for Vibration_Value X milliseconds
  Pause for Pause_Value X milliseconds
  Activate Second Motor and Right Light for Vibration_Value X milliseconds
  Pause for Pause_Value X milliseconds
  Increment Counter
  Display Count
  Goto Cycle In a single treatment "set" the operator, usually a therapist, will: (a) see that the first and second vibrating elements 20A and 20B are in contact with the subject 12, (b) turn on the power switch 50, (c) adjust the operating controls 52 to suit individual client preference, (d) monitor the visual display module 42, and (e) adjust the operating controls 52 as needed throughout the treatment set.

Accordingly, it can be seen that the device for inducing alternating tactile stimulations is simple and easy to use. It is also a preferable alternative to the current application of treatment procedures which involve therapists personally touching clients. This device offers several other advantages:

(1) A therapist can sit in a comfortable and relaxed posture instead of holding, for extended periods, the awkward postures necessary for manually tapping on the clients.

(2) A therapist can stay focused on the therapeutic process as it unfolds in the client, without also mentally counting alternating taps.

(3) Clients who might otherwise feel threatened by the therapist's touch can receive the benefits of this treatment procedure variation without additional traumatization.

(4) The non-intimate and non-personal nature of the tactile stimulations induced by the device reduces the possibly of clients of interpreting this therapy variation as a sexual overture.

(5) A therapist can adjust the device's duration and pause controls to suit the individual preferences of clients.

While the foregoing embodiments are at present considered to be preferred, it is understood that numerous variations and modifications may be made therein by those skilled in the art. For example, the size and shape of the vibrating elements may be altered to conform to the contours of the hands or other parts of a subject's body. In the case of their use by children, the vibrating elements may be embedded in an appealing toy or stuffed animal. In addition, fastening straps may be used to attach the vibrating elements to the subject's limbs or torso. There are alternatives to electric motors with off-center weights for inducing vibrations. Some of these include, but are not limited to, electromagnetic vibrators, and acoustic elements (such as speakers operated at low frequencies). Other embodiments for the controller might consist of various combinations of keypads and visual displays such as membrane switches, joysticks, dials, meters, liquid crystal displays, and computer interfaces. Additionally, the activation of the vibrating elements may be accomplished by mechanisms other than electrical wires, such as a remote control mechanism employing radio, infrared, or ultrasonic communication.

Thus the scope of the invention should be determined by the appended claims and their equivalents, rather than by the examples given.

We claim:

1. A psychotherapeutic device for administering bilateral tactile stimulation to a human subject, said psychotherapeutic device comprising:

a first vibrating element contained in a hand-held first enclosure, said vibrating element including a first electric motor constructed and arranged to rotate an off-center weight and a first lead wire connected to said first electrical motor;

a second vibrating element contained in a hand-holdable second enclosure, said vibrating element including a second electric motor constructed and arranged to rotate an off-center wight and a second lead wire connected to said second electrical motor;

said first vibrating element being constructed and arranged to be applied to the right side of a human body;

a switch-activated, battery-powered, hand-held controller for alternating a flow of electrical energy to each of said first and second vibrating elements through said first and second lead wires;

said switch-activated, battery-powered, hand-held controller constructed and arranged to activate and control a succession of activation cycles, wherein an activation cycle comprises activation of said first vibrating element for a vibration-duration time period followed by a pause-duration time period, then activation of said second vibrating element for a vibration-duration time period followed by a pause-duration time period;

said vibration-duration time period for the first and second vibrating elements extending from about 5 milliseconds to about 300 milliseconds;

said pause-duration time period for said first and second vibrating elements extending from about 50 milliseconds to about 40000 milliseconds; and said switch-activated, battery-powered, hand-held controller including a first blinking light and a second blinking light, wherein said first and second blinking lights are synchronized with the activation of the first and second vibrating elements, respectively.

2. A psychotherapeutic device as defined in claim 1 further including:

a first fastening strap for holding said first enclosure against a body part of the human subject;

a second fastening strap for holding said second enclosure against the body part of the human subject.

3. A psychotherapeutic device as defined in claim 1 wherein said first vibrating element and said second vibrating element are each embedded in a toy.

4. A psychotherapeutic device as defined in claim 1 wherein said switch-activated, battery-powered, hand-held controller provides a digital display of the number of said activation cycles.

5. A psychotherapeutic device as defined in claim 4 wherein said digital display appears on a group of LEDs.

6. A psychotherapeutic device as defined in claim 1 wherein a programmable microcontroller is used to regulate said activation cycles by alternating the flow of electrical energy between each of said first and second vibrating elements.

7. A psychotherapeutic device as defined in claim 1 wherein said switch-activated, battery-powered, hand-held controller is divided into an electrical compartment and a battery compartment.

8. A psychotherapeutic device as defined in claim 1 wherein said switch-activated, batter-powered, hand-held controller controls the flow of electrical energy to said first and second vibrating elements in a series of said activation cycles comprising:
- a vibration-duration time period of about 50 milliseconds to about 200 milliseconds; and
- a pause-duration time period of about 100 milliseconds to about 2000 milliseconds.

9. A psychotherapeutic device for administering bilateral tactile stimulation against the body of a human subject, said psychotherapeutic device comprising:
- a first hand-held, signal-activated vibrating element;
- a second hand-holdable, signal-activated vibrating element;
- said first signal-activated vibrating element being constructed and arranged to be applied to the right side of a human body;
- said second signal-activated vibrating element being constructed and arranged to be applied to the left side of a human body;
- a switch-activated, battery-powered controller, containing a programmable microcontroller to control a succession of activation cycles;
- said activation cycle including activation of said first signal-activated vibrating element for an activation period followed by a pause period, then activation of said second signal-activated vibrating element for an activation period followed by a pause period;
- said programmable microcontroller providing for said activation period from about 50 milliseconds to about 200 milliseconds and said pause period from about 100 milliseconds to about 2000 milliseconds;
- said switch-activated, battery-powered controller further including a visual display indicating which of said first and second signal-activated vibrating elements is activated.

10. A psychotherapeutic device as defined in claim 9 wherein the vibration of the first and second signal-activated vibrating elements is caused by an electric motor which rotates an off-center weight.

11. A psychotherapeutic device as defined in claim 9 wherein the vibration of the first and second signal-activated vibrating elements is caused by an electromagnetic vibrator.

12. A psychotherapeutic device as defined in claim 9 wherein the vibration of the first and second signal-activated vibrating elements is caused by an acoustic element.

13. A psychotherapeutic device as defined in claim 9 wherein the signal activating said first and second signal-activated vibrating elements is an electrical signal provided through a lead wire.

14. A psychotherapeutic device as defined in claim 9 wherein the signal activating said first and second signal-activated vibrating elements is a radio signal.

15. A psychotherapeutic device as defined in claim 9 wherein the signal activating said first and second signal-activated vibrating elements is an infrared signal.

16. A psychotherapeutic device as defined in claim 9 wherein the signal activating said first and second signal-activated vibrating elements is an ultrasonic signal.

17. A psychotherapeutic device as defined in claim 9 wherein said activation period is manually adjustable.

18. A psychotherapeutic device as defined in claim 9 wherein said pause period is manually adjustable.

19. A psychotherapeutic device as defined in claim 9 further including a display of a count of the number of times said first and second signal-activated vibrating elements have been activated.

20. A psychotherapeutic device as defined in claim 19 wherein said count of the number of times said first and second signal-activated vibrating elements have been activated is resetable by a switch said controller.

* * * * *